United States Patent [19]
Burrell et al.

[11] Patent Number: 5,124,172
[45] Date of Patent: Jun. 23, 1992

[54] THIN FILM DIAGNOSTIC DEVICE

[75] Inventors: Robert E. Burrell; Anthony G. Naylor; Aron M. Rosenfeld, all of Kingston Ontario, Canada

[73] Assignee: Alcan International Limited, Montreal, Canada

[21] Appl. No.: 498,000

[22] Filed: Mar. 23, 1990

[30] Foreign Application Priority Data

Apr. 28, 1989 [CA] Canada .................. 598172

[51] Int. Cl.⁵ .................................. A01N 1/02
[52] U.S. Cl. ........................... 427/2; 427/338; 427/404; 427/419.2; 422/55; 436/525; 435/7.1; 435/7.92; 204/192.15; 205/202
[58] Field of Search .............. 427/2, 219.2, 162, 404, 427/338, 414; 422/55, 56, 57, ; 436/525; 435/7; 204/58, 192.15

[56] References Cited

U.S. PATENT DOCUMENTS

| | | | |
|---|---|---|---|
| 3,511,661 | 5/1970 | Rauner et al. | 204/58 |
| 3,904,367 | 9/1975 | Golibersuch | 436/518 |
| 3,926,564 | 12/1975 | Giaever | 422/57 |
| 3,979,184 | 9/1976 | Giaever | 422/57 |
| 4,054,646 | 10/1977 | Giaever | 427/250 |
| 4,090,849 | 5/1978 | Healey et al. | 422/55 |
| 4,104,417 | 8/1978 | Sara | 427/404 |
| 4,172,827 | 10/1979 | Giaever | 427/250 |
| 4,190,315 | 2/1980 | Brettle et al. | 204/58 |
| 4,251,330 | 2/1981 | Sheasby et al. | 204/58 |
| 4,310,586 | 1/1982 | Sheasby et al. | 204/58 |
| 4,558,012 | 12/1985 | Nygren | 436/501 |
| 4,769,121 | 9/1988 | Newman | 427/4 |
| 4,818,710 | 4/1989 | Sutherland et al. | 356/246 |
| 4,837,061 | 6/1989 | Smits et al. | 428/40 |
| 4,891,113 | 1/1990 | Criss | 204/192.15 |
| 4,979,821 | 12/1990 | Schutt et al. | 356/246 |

OTHER PUBLICATIONS

Adams, et al.: Journal of Immunological Methods—No. 3, (1973) 227-232, "Three Simple Ways to Detect Antibody-Antigen Complex on Flat Surfaces".
Giaever, et al.: Journal of Immunology-vol. 110, No. 5, May 1973, pp. 1424-26-"The Antibody-Antigen Reaction: A Visual Observation".
Keese, et al.: Journal of Immunological Methods-43 (1981) 313-317, "Measurement of Antigen Concentrations with a One-Step Inhibition Assay".
Laffin, R. J. -Biochemical Application of Immobilized Enzymes and Proteins Chang. Ed., vol. 2, pp. 147-162.
Nygren, et al.: Journal of Immunological Methods-59, (1983) 145-149, "Direct Visual Detection of Protein Antigen: ....".
Brace and Sheasby-Technology of Anodizing Alumunum-pp. 7-8.
Rolfe, et al.: Chemistry in Britain-vol. 24, No. 10, Oct. 1988, "Medical Sensors and Biosensors".
Giaever, et al.: Proc. Nat. Acad. Sci. USA-vo. 71, No. 11, pp. 4533-35, "Visual Detection of Hepatitis B Antigen".

*Primary Examiner*—Michael Lusignan
*Assistant Examiner*—Diana L. Dudash
*Attorney, Agent, or Firm*—Cooper and Dunham

[57] ABSTRACT

A thin film diagnostic device capable of detecting the presence of a specific organic material in a sample solution. The device comprises a layer of an anodizable color-generating metal (e.g. tantalum), a porous anodic film containing aluminum oxide overlying the color generating metal, and a reagent capable of binding with the specific organic material forming a coating on the anodic film. The porous anodic film and the coating have a combined thickness such that a color change is produced when the specific organic material binds to the reagent. The device can be used to test the biological or synthetic products in samples taken from patients or other sources.

9 Claims, 3 Drawing Sheets

THIN FILM DIAGNOSTIC DEVICE

BACKGROUND OF THE INVENTION

I. Field of the Invention

This invention relates to devices used for testing for the presence of specific organic compounds in fluids and, in particular, to devices of this kind which exhibit a visible colour change when the specific compounds are detected.

II. Summary of the Prior Art

The testing of fluids, particularly body fluids, for the presence of specific biological or synthetic materials is becoming an increasingly important part of scientific procedures, particularly medical diagnosis and treatment. Such testing is often carried out in laboratories which employ sophisticated and expensive equipment. However, this is not only undesirable from the point of view of the expense, but is often time consuming and requires numerous different samples to be collected in the same place, thus giving rise to the possibility of errors in identifying the origins of the samples.

In order to avoid these disadvantages, there is a growing demand for simple but reliable tests that can be carried out at the point of origin of the samples, for example in a doctor's office, by a patient at home or at any other convenient location. A variety of tests of this type are already commonplace, e.g. it is possible to measure the sugar content of urine by observing a colour change of an absorbent paper strip dipped into the fluid. However, tests for other biological products are often difficult to simplify in this manner, and researchers have been turning to less obvious physical and chemical phenomena for incorporation into such test procedures, particularly when such phenomenona produce a readily observable change of appearance of an item.

For example, Sagax Instrument AB of Sweden were awarded U.S. Pat. No. 4,558,012 on Dec. 10, 1985 for a "Method and Member for Detecting and/or Measuring the Concentration of a Chemical Substance". In the preferred form, the detection device comprises a thin layer of $SiO_2$ on a carrier wafer, and a layer of detection reactant or counter reactant (e.g. a layer of an antibody) on the $SiO_2$ layer. Interposed between the $SiO_2$ layer and the carrier wafer is at least one additional dielectric layer. The thicknesses of the respective layers are such that interference colours are observable and, when a material to be detected (e.g. to be detected (e.g. an antigen) is trapped as a thin layer by the detection reactant or counter reactant, the interference effect is varied and a colour change is produced.

The problem with this type of device is that the interference colours are not very noticeable and the multi-layer structure is difficult and expensive to produce.

It is known that strong interference colours are produced when certain metals (e.g. Ta) are anodized at high voltages. The anodization causes a thin barrier film of metal oxide to grow at the metal surface and the thickness of the film is such that reflections from the surface of the film and reflections from the underlying metal interfere and generate highly visible colours. Structures of this type are candidates for diagnostic devices because the observed colour is highly dependent on the thickness of the transparent film and small changes in thickness can produce noticeable colour changes. This phenomenon was suggested for use in diagnostic devices by Adams, Kings, Fischer and Vroman in the Journal of Immunological Methods 3(1973) 227-232. In this case, Ta was sputtered onto glass, the Ta was anodized and a bronze colour was observed. The anodized Ta was then coated with a protein and exposed to an antigen-antiserum mixture. The colour changed to reddish purple when a monolayer of antigen was absorbed and this colour changed to deep violet when covered with antibody.

Despite the apparent success in applying anodic interference colours to diagnostic devices reported above, we have found that the colour changes produced in such structures by the adsorption of thin organic layers are not readily observable and are difficult to utilize in practice Accordingly, there is a need for improved structures capable of exhibiting noticeable colour changes when coated with thin organic films.

SUMMARY OF THE INVENTION

The present invention is based on the finding that an improved diagnostic interference device can be produced by utilizing an anodized metal film structure comprising a porous layer of aluminum oxide overlying a non-aluminum anodizable metal. The aluminum oxide has an index of refraction close to that of protein for high sensitivity and the porosity of the oxide can be adjusted to tune the index to optimise the sensitivity. The oxide film is formed by anodization leading to an inexpensive process with precise thickness control for high reproducibility and uniformity. The aluminum oxide surface as fabricated allows strong binding of a range of proteins of interest for immuno-assay, without the need for intermediate chemical treatments. The porous nature of the aluminum oxide results in two effects, first an effective refractive index change in the dielectric when protein is bound within the film and second an enhanced area for binding of protein to the surface of the film. Both of these effects act to change the optical thickness of the dielectric and result in a colour change when organic molecules such as protein are bound to the surface.

Thus, according to one aspect of the invention there is provided a thin film diagnostic device capable of detecting the presence of a specific organic material in a sample solution, said device comprising: a layer of an anodizable metal capable of generating a colour when covered by a transparent layer of suitable thickness; a porous anodic film comprising aluminum oxide overlying said colour-generating metal; and a reagent capable of binding with said specific organic material from said sample solution forming a coating on said anodic film; said porous anodic film and said coating having such a combined thickness that a colour change is produced when said specific organic material binds to said reagent.

According to another aspect of the invention there is provided a process for producing a thin film diagnostic device capable of detecting the presence of a specific organic material in a sample solution, said process comprising: providing a layer of an anodizable metal capable of generating a colour when covered by a transparent layer of suitable thickness; providing a coating of a material selected from the group consisting of aluminum and anodizable aluminum alloys on said metal capable of generating a colour to a thickness suitable, following conversion to an oxide of said material, for colour generation; porous anodizing said material to consumption to form a porous anodic film; and coating the resulting porous anodic film with a reagent capable of binding with said specific organic material from said sample solution.

According to yet another aspect of the invention there is provided apparatus for viewing a thin film diagnostic device, comprising a hollow elongated body having a viewing window at one longitudinal end, a light deflecting surface at an opposite longitudinal end, an opening to permit the entry of light and a support within said body capable of supporting said thin film diagnostic device, said light deflecting surface being positioned and orientated to deflect light entering said opening onto said device, and said window being positioned to view said light reflected from said device.

Figure 1:
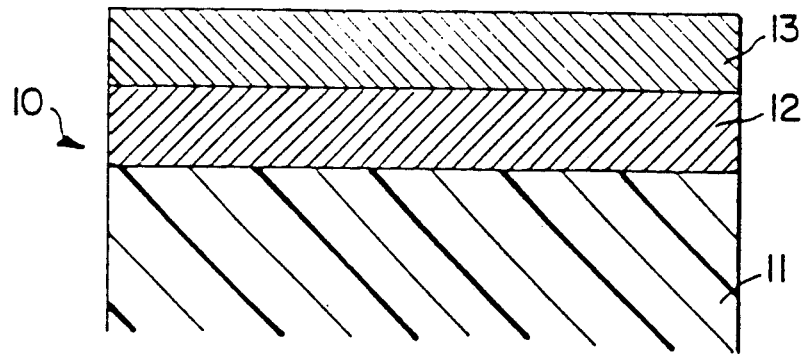
FIG. 1 is a cross-section of a structure having a layer of aluminum overlying a tantalum layer on a substrate.

It should be noted that relative dimensions of the various layers and other items shown in the drawings are not intended to be to scale.

DETAILED DESCRIPTION OF THE INVENTION

The present invention is based on the creation of a colour change when a target organic material binds to a structure capable of generating a colour by interference (and light absorption) effects. As previously mentioned in connection with the prior art, certain metals are capable of generating such colours when covered with extremely thin transparent layers. Changes in thickness of the transparent layers, if large enough, produce noticeable changes in the hue of the generated colour. When the change of effective optical thickness exceeds about 2.5%, a noticeable colour change is produced.

More accurately, the parameter which determines the particular colour exhibited by the structure is the "effective optical thickness" of the transparent layer, i.e. the product of the index of refraction of the transparent material and the actual thickness of the transparent layer. Consequently colour changes can be produced either by a change in the actual thickness of the transparent layer, or by a change of the refractive index of the layer, or by a combination of the two.

When a reagent material is adhered to a non-porous anodic film, the reagent coating increases the physical thickness of the transparent film overlying the colour-generating metal. When the anodic film is porous the reagent coating increases the thickness of the film, and if the reagent penetrates the pores, the refractive index of the transparent film overlying the colour generating metal is also changed. When a target organic material binds to the reagent material, similar changes in thickness and average refractive index are caused and these changes result in a colour change. In practice, however, the reagent coating and the target organic material layer may each have the thickness of only a single molecule so that the resulting changes of thickness for a non porous surface may be insufficient to produce noticeable colour changes. In the present invention, the anodic film is porous (at least at its outer surface) and this has the effect of increasing the surface area to which the reagent material and target organic material can bind, and also of producing both thickness and refractive index changes. This enhances the amount of colour change and it is possible to maximize (or "tune") the colour change for each particular reagent-organic material combination by choosing an appropriate thickness and/or porosity of the anodic film to best exploit the particular optical or other significant properties of each combination.

The colour-generating metals which may be employed in the present invention include the so-called valve metals, e.g. Ta, Nb, Ti, Zr and Hf, as well as transition metals such as V, W and Mo. These are all metals which generate colours not only by simple interference effects but also by virtue of the fact that some of the light striking the metal surface is absorbed and therefore the intensity of the reflected light is more comparable with the light reflected from the transparent layer so that interference is maximized. While the colour-generating metals may be used in the form of plates, foils, shaped objects etc., their relatively high cost makes it more economical to use the metals in the form of very thin layers supported on suitable substrates. A layer of only a few hundred Angstrom units in thickness can easily be formed on a suitable substrate by sputtering, evaporation or other techniques. In general, the metal layer should be at least 250 Å in thickness in order to provide the required colour-generating properties.

In the process of the present invention, the colour-generating metal is coated with a layer of aluminum or anodizable aluminum alloy, preferably also by a sputtering or evaporation technique, or by any other suitable method. The thickness of the aluminum layer is preferably in the range of 600-2400 Å because this produces a porous oxide layer, following the anodizing step, capable of providing a range of interference colours spanning the first to the fourth orders. A layer having the optimum thickness can be provided in each case bearing in mind that first and second order colours have been shown to be extremely sensitive to the precise thickness of the transparent layer and changes resulting from a difference in thickness of only 25Å are readily detectable by the eye in some colour ranges.

The aluminum layer may consist of pure aluminum or any anodizable aluminum alloy, e.g. any of the alloys listed in Table 1 on page 7 of "The Technology of Anodizing Aluminum" by A. W. Brace and P. G. Sheasby, Technicopy Limited, Gloucester, England, the disclosure of which is incorporated herein by reference. For the sake of simplicity, the aluminum or aluminum alloy layer is referred to in this disclosure simply as an "aluminum" layer so it should be understood that this term encompasses anodizable aluminum alloys.

Once the aluminum layer has been deposited, it is subjected to porous anodization. This may be carried out at a voltage of up to 150V. The anodization is generally carried out at ambient temperatures in an electrolyte containing a suitable acid, e.g. sulphuric acid, phosphoric acid or oxalic acid, or mixtures thereof. The anodization is continued until the aluminum layer is completely consumed and the current has dropped to near zero, indicating the formation of a thin non-porous barrier layer of oxide on the colour-generating metal surface. The porous layer is normally washed and dried before being coated with the reagent material.

The reagent material used in the present invention may be either member of a pair of molecules that selectively bind together to form a complex. Examples of such pairs are antibody-antigen, enzyme-substrate, enzyme-receptor, toxin-receptor, protein-protein, and avidin-biotin. Since monoclonal antibodies specific to a wide variety of antigens can now be produced without great difficulty, the use of one member of an antibody-antigen pair is most preferred. Examples of suitable antibodies include those from the classes IgG (e.g. anti-prothrombin, antihuman chorinic gonadotropin, anti-antibiotics and anti-anti HIV (AIDS)), IgM and IgE. By suitably selecting the reagent materials, diagnostic devices suitable for testing for a large variety of natural biological materials (products or by-products of metabolism) as well as synthetic materials (such as anti-biotics, illicit drugs, etc.) can be developed.

The reagent material can be coated relatively easily on the anodic film, e.g. by dissolving the reagent in a suitable solvent, coating the solution onto the film, allowing the coated film to stand, e.g. for up to 24 hours, and then removing excess coating solution, e.g. by washing with a buffer solution, and then drying the coated film. The reagent normally adheres quite strongly to the porous anodic film by adsorption, but standard protein binding techniques may also be used. Antibodies bind quite strongly to the anodic film while other proteins bind with varying strengths. For example, vitamin K dependent proteins such as prothrombin have a particularly high affinity for aluminum oxide surfaces and in fact are routinely removed from plasma by adsorption to these surfaces in clinical chemistry laboratories.

The initial colour of the test device of the invention is dependent upon the type of colour-generating metal employed, the thickness and refractive index of the transparent layer (anodic film plus reagent coating), the angle of incident light and the state of polarization. All of these can be selected to optimize the response of the device. Indeed, the device may initially appear colourless, provided a colour is produced when the target molecule binds to the device so that the required noticeable colour change is produced.

The device of the invention is normally viewed in white light, but coloured light containing several wavelengths of different intensity, and also monochromatic light may be used instead. Any device which produces a colour change in light containing more than one wavelength produces a change of intensity in monochromatic light of the appropriate wavelength and this change of intensity can be used to detect the target material. Consequently, the term "colour change" as used herein is intended to include changes of intensity of the light under monochromatic light as well as change of hue observed from white light containing more than one wavelength. Changes of light intensity can be measured very sensitively by known apparatus (e.g. a photometer) and changes in color not easily detectable by the naked eye can be measured by known apparatus (e.g. a spectrophotometer). However, even for the naked eye, the contrast between the original colour and the colour following exposure to the material to be detected can usually be enhanced by illuminating the surface with a non white light source containing the appropriate range of wavelengths. The colour of the light source (i.e. the number and intensity of the wavelengths contained) producing maximum contrast will depend on the interference colour and the angle of observation. A simple method of achieving this effect is to place the surface to be observed against a coloured background, and view the background reflected in the surface. Correct choice of the background gives rise to a large increase in contrast between the original colour and the target material layer colour.

When observing the colour change without resorting to sophisticated equipment, it has been found that in some cases the maximum sensitivity is obtained by viewing at other than normal incidence (90°). The optimal viewing angle is determined by the voltage of anodizing and the thickness of the anodic film which is preselected for the specific end use. The interference effect of thin films is angular dependent because the change of colour observed when a target material binds to the device is dependent on the optical thickness of the transparent layer (i.e. the refractive index multiplied by the physical thickness). The effective optical thickness increases as the angle of incidence of the light falling on the surface increases and the ratio of the reflected to the refracted light increase. The colour observed consequently depends on the angle at which the surface is observed. Also the interference effect at all angles except 90° is different for the p and s polarizations, so that a polarizing filter can be used to block out light that has a less observable change.

When using the test device of the invention, the device can be dipped into a sample fluid or a drop of the fluid can be dropped onto the porous surface of the device. After an appropriate time to allow binding to take place, the sample fluid can be washed off and the device allowed to dry. The device is then viewed in the manner stated to check for any observable colour changes.

For a further understanding of the invention, examples of structures embodying the present invention and apparatus for viewing the colour change effects are shown in the accompanying drawings.

FIG. 1 is a cross-section of a layered structure 10 consisting of a substrate 11 made, for example, of glass or plastic, a thin sputtered layer 12 of tantalum, and a layer 13 of sputtered aluminum. The layer 12 is thick enough to ensure that at least 250Å remains unconsumed after the anodization step in order to guarantee the generation of the desired colour. The thickness of the aluminum layer 13 must be such that, following its anodization, it is also appropriate for generating the required colour, and thicknesses up to 3000Å (following anodization) are normally suitable.

Figure 2:
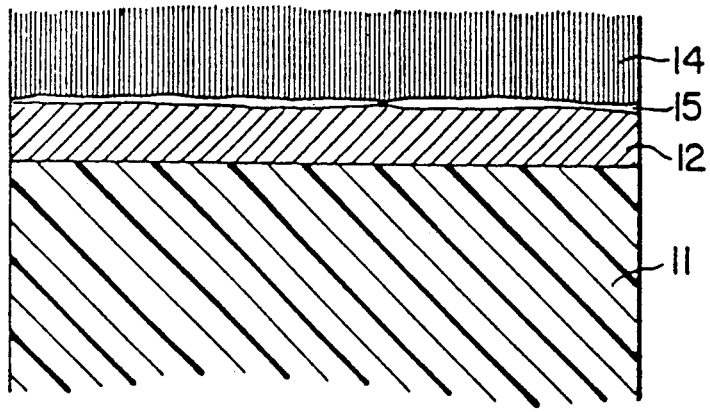
FIG. 2 is the device of FIG. 1 following porous anodization of the aluminum layer.
Figure 3:
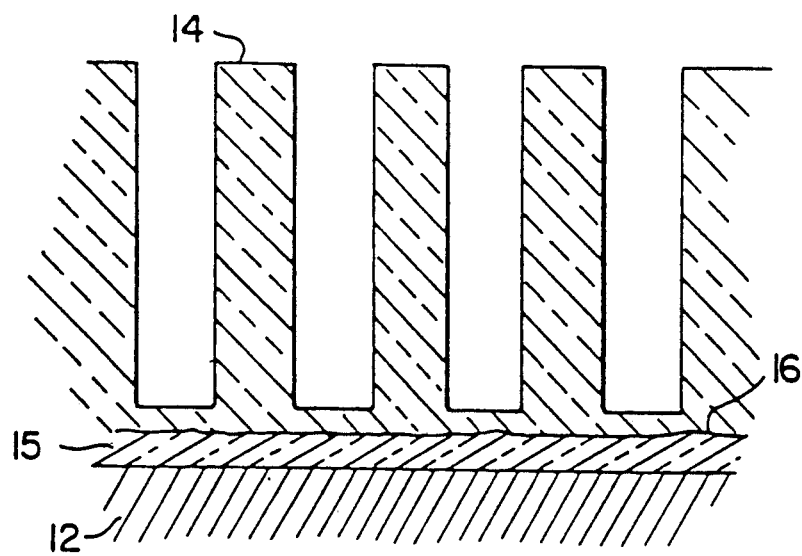
FIG. 3 is an enlarged view of part of the porous layer of FIG. 2.

FIGS. 2 and 3 show the structure following the porous anodizing step. The aluminum layer 13 of FIG. 1 has been completely converted into a porous anodized aluminum oxide-containing layer 14. The anodization has also consumed some of the tantalum at the upper surface of the tantalum layer 12 to form a very thin barrier layer 15 of tantalum oxide.

Figure 4:
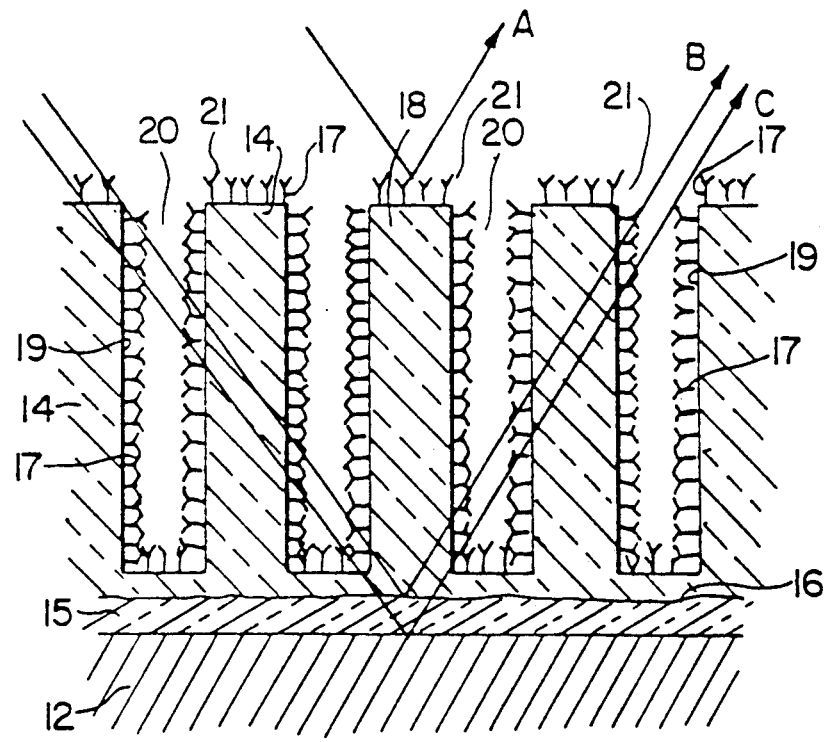
FIGS. 4 and 5 are enlarged views similar to FIG. 3 showing layers of antibody and antigens attached to the structure.

As shown in FIG. 4, following the anodization step, a reagent material, described hereinafter as an antibody, is applied to the surface of the porous anodized layer 14 to form a coating 17 (which may be only a single molecule thick). The coating 17 covers both to the outer surfaces 18 of the porous layer and also the interior surfaces 19 of pores 20.

The resulting structure is capable of generating a colour by a light interference and absorption effect as shown in FIG. 4. Light reflected from the upper surface 21 of the antibody-coated porous layer 14 (ray A) interferes with light reflected from an interface 16 between the aluminum and tantalum oxides (ray B) and the upper surface of the metal 12 (ray C). This interference is enhanced by light absorption which takes place at the tantalum metal/tantalum oxide interface, which has the effect of making the intensities of rays A, B and C more equal so that their mutual interference is stronger and the generated colours are more intense. This absorption effect is characteristic of the colour-generating metals mentioned above and is the reason why these metals are capable of generating such intense colours.

Figure 5:
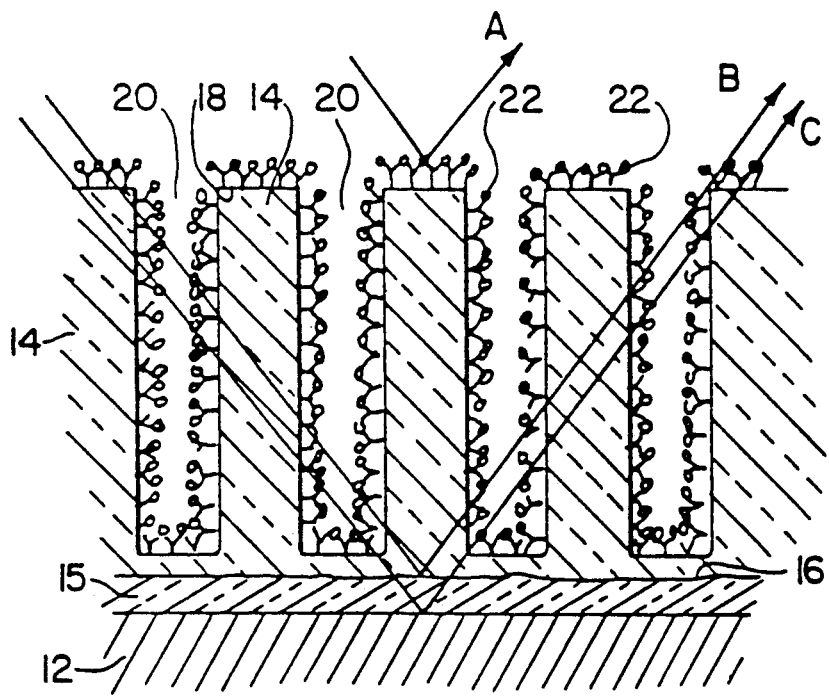

FIG. 5 shows the same structure as FIG. 4 but following immersion in a fluid sample containing an antigen for the antibody. The antigen becomes tightly attached to the antibody to form an antibody-antigen complex. Thus a second coating 22 is formed on the porous layer and this affects the optical properties of the structure in two ways. Firstly, because the coating 22 enters the pores 20, it changes the average refractive index of the layer 14. Secondly, since the antigen has also bonded to the antibody on the outer surface 18 of the layer 14, it has effectively increased the physical thickness of this layer. Both these changes increase the effective optical thickness of the layer 14, and a noticeable colour change is produced. The colour change consequently demonstrates the presence of the antigen in the sample fluid. Since the antibodies will bind only with one particular antigen, the test device is very selective as well as being sensitive.

As noted previously, the colour change can be even more noticeable if (1) the device is viewed at a low angle, (2) a polarizing filter is employed to view the sample and is rotated to the optimum orientation, and (3) the sample is viewed in the optimum coloured light containing several wavelengths. FIGS. 6 (a) and (b) show two devices which facilitate these effects.

Figure 6A:
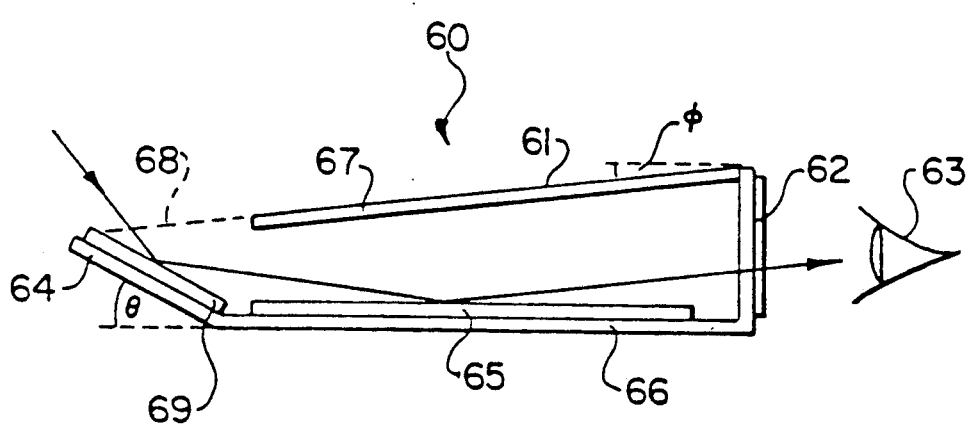
FIGS. 6 (a) and (b) are cross-sections of viewing devices designed to make the colour changes more readily visible.

The apparatus 60 shown in FIG. 6(a) consists of a box 61 having a viewing window 62 at one end permitting an observer 63 to look into the box along its longitudinal axis. The wall 64 of the box opposite to the window 62 is arranged at an angle 8 to the horizontal. The angle $\theta$ is chosen to reflect the maximum light from a suitable source (e.g. overhead light, desk lamp, window, etc.) onto a device 65 according to the invention positioned horizontally within the box along the lower wall 66. The angle $\theta$ is usually in the range of 15°–50°. The upper wall 67 of the box is arranged at an angle $\phi$ below the horizontal. This angle $\phi$ is chosen in accordance with the size of the window 62 and the length of the bottom wall 66 such that only light striking end wall 64 will be reflected from the device 65 to the eye of the observer. The window 62 is preferably polarizing and can be rotated. The orientation of the window is chosen to give the maximum intensity differential between reacted and unreacted parts of the device 65 (normally drops of the sample solution are placed on the test device 65 and are then wiped off, producing reacted and unreacted parts of the device). Opening 68 (which is large enough to permit insertion and removal of the device 65) may optionally be covered with a transparent cover (not shown) which may be coloured to act as a filter to transmit coloured light into the interior of the box for viewing of the device. End wall 64 may be provided with a reflective device 69, which may be a top surface coated reflective mirror (e.g. silver or aluminum coated), a bottom surface coated mirror with a coloured filter formed by staining the mirror substrate glass or plastic, or a thin film reflective mirror, the film thickness being chosen to form a dichroic mirror giving the selected colours at the particular angle of reflected light.

Figure 6B:
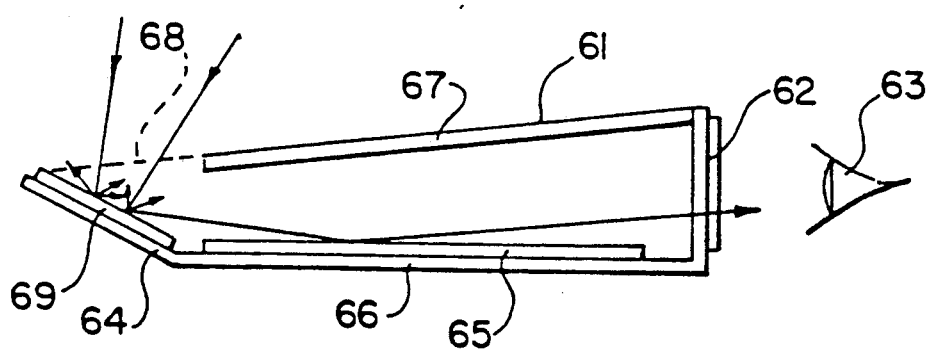

The apparatus shown in FIG. 6(b) is similar to the apparatus of FIG. 6(a) except that device 69 is in this case a reflective light diffusing surface rather than a direct reflecting surface. A white or coloured surface may be employed.

EXAMPLE 1

This example illustrates the sensitivity of this type of detector, as denoted by a visible colour change, to very small thickness changes. The changes were due to the controlled deposition of an organic Langmuir-Blodgett (L-B) film on the detector surfaces.

Detectors of the type shown in FIGS. 2 or 3 were formed by sputtering tantalum to a thickness of 2000 Å onto a glass support, then sputtering aluminum to a thickness of 1800 Å on the Ta, anodizing the aluminum at 20 V in an electrolyte containing 0.4M $H_3PO_4$ to produce an anodized layer comprising 2400 Å of $Al_2O_3$ and 340Å of $Ta_2O_5$. The colour of the resulting detectors when observed in white light were red.

After the addition of an L-B film of stearic acid, having a thickness of 27Å, the colour changed to diffuse purple. Thus these detectors are sensitive to thickness changes of as little as 27Å.

EXAMPLE 2

This example illustrates that multiple colour and intensity shifts are observed when the thickness of an organic layer is increased on the surface of the detector.

Detectors identical to those of Example 1 were formed. One was coated with an L-B film of stearic acid (27 Å). This resulted in a colour change from red to diffuse purple. Another detector was coated with five stacked L-B coatings of stearic acid to a total thickness of 135Å. The colour changed from red to deep purple. It is clear that as the thickness of the organic film changed so did both the colour and intensity of colour generated.

EXAMPLE 3

This Example illustrates the detection of an adsorbed layer of protein (specifically an IgG antibody).

Three different detectors were produced according to the following:

| | Detector | | |
|---|---|---|---|
| Parameter | A | B | C |
| Al thickness | 1800 Å | 2200 Å | 1200 Å |
| Ta thickness | 2000 Å | 2000 Å | 2000 Å |
| Support | glass | glass | glass |
| Anodizing conditions | 20 V; 0.4M $H_3PO_4$ | 4 V; 0.4M $H_3PO_4$ | 4 V; 0.4M $H_3PO_4$ |
| $Al_2O_3$ thickness | 2400 Å | 2860 Å | 1560 Å |
| $Ta_2O_5$ thickness | 340 Å | 68 Å | 68 Å |
| Colour (75° from normal) | yellow | tan | tan |
| Colour (15° from normal) | red | colourless | colourless |

The detectors were each coated with 2-4 $\mu g/cm^2$ (nominal surface area) of IgG (rabbit raised antiprothrombin). The detectors were viewed at angles of 15° from normal and 75° from normal and the following results were observed.

| Viewing Angle | Detector Colour Changes | | |
|---|---|---|---|
| | A | B | C |
| 15° from normal | red → dark purple | no change | no change |
| 75° from normal | yellow → blue | tan → dark purple | tan → dark purple |

When IgG was added to these types of detectors a colour change was observed. This indicated that the protein was adsorbed and it changed the optical thickness of the film.

EXAMPLE 4

This Example illustrates the detection of an adsorbed layer of protein (not an antibody).

Detectors identical to those in Example 3 were formed and each was coated with 3-7 pg/cm$^2$ (nominal surface area) of human prothrombin. The detectors were viewed at 15° and 75° from normal and the following colour changes were observed.

| Viewing Angle | Detector Colour Changes | | |
|---|---|---|---|
| | A | B | C |
| 15° from normal | red → dark purple | no change | no change |
| 75° from normal | yellow → blue | tan → light purple | tan → light purple |

When a protein (not an antibody) is adsorbed to the detector, a colour change occurs. This indicated that the adsorbed protein changes the optical thickness of the film.

EXAMPLE 5

This Example illustrates how the thin film detectors of the invention can be used to detect antigens in solution. This is accomplished by capturing specific antigens on antibodies immobilized on the surface of the detector.

Two detectors were produced as follows:

| Parameter | Detector | |
|---|---|---|
| | A | B |
| Al thickness | 2200 A | 1200 A |
| Ta thickness | 2000 A | 2000 A |
| Support | glass | glass |
| Anodizing conditions | 40 V; 0.4M H$_3$PO$_4$ | 4 V; 0.4M H$_3$PO$_4$ |
| Al$_2$O$_3$ thickness | 2860 A | 1560 A |
| Ta$_2$O$_5$ thickness | 68 A | 68 A |
| Colour (15° from normal) | colourless | colourless |
| Colour (75° from normal) | tan | tan |
| Protein Layer | 4.6 μg IgG*/cm$^2$** | 2-3 μg IgG*/cm$^2$** |
| Colour (15° from normal) | Purple | Purple |
| Colour (75° normal) | Colourless | Colourless |

*IgG antiprothrombin
**nominal surface area

The detectors were coated with a liquid containing 100 μg prothrombin per mL. After a 30 minute incubation period the excess liquid was removed and the slide was air dried. The dry slide was then viewed at 75° from normal and the following colour change was observed.

| Viewing Angle | Detector Colour Changes | |
|---|---|---|
| | A | B |
| 75° from normal | purple → blue | purple → blue |

This demonstrated the detection of an immune complex when the adsorbed protein was an antibody. It also demonstrated that both first order (detector B) and second order (detector A) colour generating films can be used for detection of immune complexes.

EXAMPLE 6

This Example illustrates the use of the thin films of the invention for the detection of immunocomplexes when an antibody is adsorbed to the surface in conjunction with a surface blocking agent such as bovine serum albumin.

Several detectors were produced, as follows:

| Al thickness | 1200 A |
|---|---|
| Ta thickness | 2000 A |
| Support | glass |
| Anodizing conditions | 4 V; 0.4M H$_3$PO$_4$ |
| Al$_2$O$_3$ thickness | 1560 A |
| Ta$_2$O$_5$ thickness | 68 A |
| Colour (75° from normal) | tan |
| Protein 1 | antiprothrombin (3 μg/cm$^2$) or non-immune IgG (3 μg/cm$^2$*) |
| Protein 2 | bovine serum albumin (800 μg/mL) |
| Colour (15° from normal) | deep blue |

*nominal surface area

The detectors were exposed to a solution of prothrombin (100 μg/mL) for 15 minutes. Excess material was removed and the slide was washed and dried. When viewed at 75° from normal the colour where the immune complex formed (i.e. antiprothrombin coated surface) was light blue. The control surface (i.e. nonimmune IgG) showed no colour change.

This demonstrated the detection of an immune complex when the protein adsorbed to the surface is an antibody and when a second protein (bovine serum albumin) is used to mask the surface.

EXAMPLE 7

This Example illustrates the use of these films for detection of immuno complexes when an antigen is adsorbed to the surface.

Several detectors were produced, as follows:

| Al thickness | 1200 A |
|---|---|
| Ta thickness | 2000 Å |
| Support | glass |
| Anodizing conditions | 4 V; 0.4M H$_3$PO$_4$ |
| Al$_2$O$_3$ thickness | 1560 Å |
| Ta$_2$O$_5$ thickness | 68 Å |
| Colour (75° from normal) | tan |
| Protein | prothrombin (5 μg/cm$^2$) |
| Colour | deep blue |

The detectors were exposed to a solution of antiprothrombin (100 μg/mL) of nonimmune IgG (100 μg/mL) for 15 minutes. Excess material was removed and the slides were washed and air dried. When viewed at 75° from normal the colour where the immune complex formed (i.e. exposure to antiprothrombin) changed to light blue while the control areas (non-immune IgG) did not change colour. This demonstrates the use of these slides to monitor antibody levels in a solution through an immune complexation with an immobilized antigen.

EXAMPLE 8

This Example illustrates how the device can be tuned through modulation of the non-porous/porous structure of the thin film device. This allowed the differentiation of adsorbed protein layers through control of the interference pattern generated.

A number of detectors were produced according to the following:

| Parameter | Detector A | Detector B |
|---|---|---|
| Al thickness | 2000 A | 2000 A |
| Ta thickness | 1500 A | 1500 A |
| Support | bright foil | bright foil |
| Anodizing conditions | 4 V; 0.4M $H_3PO_4$ | 20, 0.4M $H_3PO_4$ |
| $Al_2O_3$ thickness | 2600 A | 2600 A |
| $Ta_2O_5$ thickness | 68 A | 340 A |
| Colour (15° from normal) | tan | dark tan |
| Colour (75° from normal) | blue | blue/grey |

Solutions containing 500 μg/mL of either human serum albumin (globular; 68,000 MW), human prothrombin (cylindrical (108 × 27A; 68,000 MW), a rabbit IgG (globular; 150,000 MW) were added in 10 μL portions to a clean portion of surface on each detector. The colour changes observed for each protein were as follows:

| Protein | Detector Colour Changes (75° from normal) A | B |
|---|---|---|
| human serum albumin | → crimson | → light grey |
| prothrombin | → light blue | → very light grey |
| IgG | → medium blue | → medium grey |

These colour changes indicate that various proteins can be made to generate different signals bound to various thin film detectors. This is related to the inherent characteristics of each protein (dimensions, molecular weight, binding affinity, binding orientation) and the physical configuration of the thin film detector).

Those surfaces coated with prothrombin were subsequently coated with a solution of either anti-prothrombin (100 μg/mL) or non-immune IgG (100 μg/mL). Those areas coated with antiprothrombin generated a new colour while those exposed to non-immune IgG did not. This clearly demonstrated a colour shift which is due to the formation of an immune complex on the surface.

What we claim is:

1. A process for producing a thin film diagnostic device capable of detecting the presence of a specific organic material in a sample solution, said process comprising:
   providing a layer of an anodizable metal capable of generating a colour when covered by a transparent layer of suitable thickness;
   providing a coating of a material selected from the group consisting of aluminum and anodizable aluminum alloys on said metal capable of generating a colour to a thickness suitable, following conversion to an oxide of said material, for colour generation;
   porous anodizing said material to consumption to form a porous anodic film; and coating the resulting porous anodic film with a reagent capable of binding with said specific organic material from said sample solution.

2. A process according to claim 1 wherein said anodization is carried out at a voltage of up to 150V.

3. A process according to claim 1 wherein said anodization is carried out at a voltage of from 4 V to 20 V.

4. A process according to claim 1 wherein said anodization is carried out in an electrolyte containing an acid selected from the group consisting of phosphoric acid, sulfuric acid, oxalic acid and mixtures thereof.

5. A process according to claim 1 wherein said layer of anodizable metal capable of generating a colour is provided by sputtering or evaporating said anodizable metal onto a suitable support.

6. A process according to claim 1 wherein said coating of said material is provided on said metal capable of generating a colour by a sputtering or evaporating technique.

7. A process according to claim 1 wherein said reagent is coated on said porous anodic film by forming a solution of said reagent in a suitable solvent, coating the solution onto the porous anodic film, allowing the coated solution to stand and then removing the coated solution from the porous anodic film.

8. A process according to claim 1 wherein said anodizable metal capable of generating a colour is selected from the group consisting of Ta, Nb, Ti, Zr, Hf, V, W and Mo.

9. A process according to claim 1 wherein said reagent is one member of a binding pair selected from the group consisting of antibody-antigen, enzyme-substrate, enzyme-receptor, toxin-receptor, protein-protein and avidin-biotin.

* * * * *